(12) United States Patent
Tomikawa et al.

(10) Patent No.: US 11,932,644 B2
(45) Date of Patent: Mar. 19, 2024

(54) CARBAMATE ESTER COMPOUND AND ACRYLIC RUBBER COMPOSITION CONTAINING THE SAME

(71) Applicant: UNIMATEC CO., LTD., Tokyo (JP)

(72) Inventors: Yoichiro Tomikawa, Ibaraki (JP); Satoru Saito, Ibaraki (JP)

(73) Assignee: UNIMATEC CO., LTD., Tokyo (JP)

( * ) Notice: Subject to any disclaimer, the term of this patent is extended or adjusted under 35 U.S.C. 154(b) by 209 days.

(21) Appl. No.: 17/295,186

(22) PCT Filed: Nov. 14, 2019

(86) PCT No.: PCT/JP2019/044669
§ 371 (c)(1),
(2) Date: May 19, 2021

(87) PCT Pub. No.: WO2020/105536
PCT Pub. Date: May 28, 2020

(65) Prior Publication Data
US 2022/0009934 A1    Jan. 13, 2022

(30) Foreign Application Priority Data
Nov. 20, 2018   (JP) .................. 2018-217626

(51) Int. Cl.
| C07D 487/04 | (2006.01) |
| B29C 39/00 | (2006.01) |
| B29C 48/00 | (2019.01) |
| C07C 271/06 | (2006.01) |
| C07C 271/10 | (2006.01) |
| C07C 271/12 | (2006.01) |
| C08K 5/205 | (2006.01) |
| C08K 5/3462 | (2006.01) |
| C08L 13/00 | (2006.01) |
| B29K 19/00 | (2006.01) |

(52) U.S. Cl.
CPC .......... *C07D 487/04* (2013.01); *B29C 39/003* (2013.01); *B29C 48/022* (2019.02); *C07C 271/06* (2013.01); *C07C 271/10* (2013.01); *C07C 271/12* (2013.01); *C08K 5/3462* (2013.01); *C08L 13/00* (2013.01); *B29K 2019/00* (2013.01)

(58) Field of Classification Search
CPC ..... C08K 5/205; C07C 271/06; C07C 271/10; C07C 271/12; C09D 487/04
See application file for complete search history.

(56) References Cited

U.S. PATENT DOCUMENTS 3,962,302 A * 6/1976 Rosenthal ............. C07C 263/04
560/24
6,015,860 A   1/2000 Kuzumaki et al.
(Continued)

FOREIGN PATENT DOCUMENTS

CN   101932556      12/2010
CN   103059250 A     4/2013
(Continued)

OTHER PUBLICATIONS

EESR issued in EP Patent Application No. 19886367.2, Jun. 15, 2022.
(Continued)

*Primary Examiner* — Vickey Nerangis
(74) *Attorney, Agent, or Firm* — GREENBLUM & BERNSTEIN, P.L.C.

(57) ABSTRACT

A carbamate ester compound represented by the general formula:

$$Z-OCONH(CH_2)_nNHCOO-Z \qquad [I]$$

wherein Z is [i], [ii], or [iii] below, and n is an integer of 2 to 10,

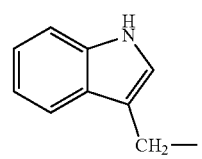

(i)

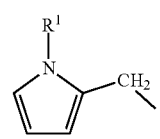

(ii)

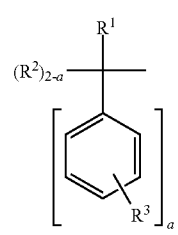

(iii)

(wherein $R^1$ and $R^2$ are each independently a lower alkyl group having 1 to 5 carbon atoms, $R^3$ is a hydrogen atom or a lower alkyl group having 1 to 5 carbon atoms, and a is 1 or 2). The carbamate ester compound is used as a vulcanizing agent for carboxyl group-containing acrylic rubber and improves the delay of the vulcanization rate by scorch suppression.

9 Claims, No Drawings

(56) References Cited

U.S. PATENT DOCUMENTS

| | | | | |
|---|---|---|---|---|
| 8,288,483 | B2* | 10/2012 | Ito | C07C 317/18 |
| | | | | 525/347 |
| 9,062,188 | B2* | 6/2015 | Koga | C08L 33/06 |
| 9,528,015 | B2* | 12/2016 | Chopra | C09D 11/34 |
| 2005/0222341 | A1 | 10/2005 | Aimura et al. | |
| 2007/0142510 | A1 | 6/2007 | Ono et al. | |
| 2011/0040043 | A1 | 2/2011 | Ito et al. | |
| 2017/0226254 | A1 | 8/2017 | Mori | |

FOREIGN PATENT DOCUMENTS

| | | |
|---|---|---|
| JP | H07-145164 | 6/1995 |
| JP | 11-100478 | 4/1999 |
| JP | 11-140264 | 5/1999 |
| JP | 11-255997 | 9/1999 |
| JP | 2001-181464 | 7/2001 |
| JP | 2001-316554 | 11/2001 |
| JP | 2002-317091 | 10/2002 |
| JP | 2003-342437 | 12/2003 |
| JP | 2004-269873 | 9/2004 |
| SU | 791742 | 12/1980 |
| WO | 2003/004563 | 1/2003 |
| WO | 2005/103143 | 11/2005 |
| WO | 2009/096545 | 8/2009 |
| WO | 2016/052335 | 4/2016 |

OTHER PUBLICATIONS

Langanke, J. et al., "Improving the scratch resistance of sol-gel metal oxide coatings cured at 250° C. through use of thermogenerated amines", Journal of Sol-Gel Science and Technology, vol. 67, No. 2, 2013, pp. 282-287.

ISR issued in WIPO Patent Application No. PCT/JP2019/044669, Feb. 18, 2020, English translation.

Written Opinion issued in WIPO Patent Application No. PCT/JP2019/044669, dated Feb. 18, 2020, English translation.

IPRP issued in WIPO Patent Application No. PCT/JP2019/044669, May 25, 2021, English translation.

* cited by examiner

CARBAMATE ESTER COMPOUND AND ACRYLIC RUBBER COMPOSITION CONTAINING THE SAME

TECHNICAL FIELD

The present invention relates to a novel carbamate ester compound and an acrylic rubber composition containing the same. More particularly, the present invention relates to a carbamate ester compound that is used as a novel vulcanizing agent for carboxyl group-containing acrylic rubber, and an acrylic rubber composition containing the same.

BACKGROUND ART

Among acrylic rubbers, carboxyl group-containing acrylic rubber particularly has excellent heat resistance and compression set characteristics, and is halogen-free acrylic rubber that is taken non-corrosiveness to metal, and is environment friendly. For this reason, demands for application of this rubber to hoses, sealing materials, etc., have been increasing in recent years. However, the scorch time is shorter with respect to the vulcanization rate; that is, the scorch time tends to be too short when the vulcanization rate is accelerated, and the scorch time tends to be longer when the vulcanization rate is slowed.

More specifically, when the vulcanization rate is accelerated to a satisfactory level, the scorch time is short, the compound flow is deteriorated, and molding failure occurs. When the vulcanization rate is slowed, the molding time increases, thereby leading to an increase in cost. This suggests that the moldability is inferior in view of the ideal that the vulcanization rate is high and the scorch time is long.

As methods for vulcanization molding of acrylic rubber, molding with mold (injection molding, compression molding, transfer molding, etc.) and extrusion molding are generally used. Currently, in order to balance the vulcanization rate during molding and the scorch time, there are the following two vulcanization systems:

(1) Aliphatic diamine (vulcanizing agent)/guanidine (vulcanization accelerator)
(2) Aromatic diamine (vulcanizing agent)/guanidine (vulcanization accelerator)

The aliphatic diamine vulcanization system used for molding with mold application, which mainly gives priority to the vulcanization rate, has a higher vulcanization rate and a shorter scorch time than those of the aromatic diamine vulcanization system used for extrusion molding application, which mainly gives priority to the scorch time (t5: 10 minutes or more). In contrast, the aromatic diamine vulcanization system (4,4'-diaminodiphenyl ether, 2,2-bis[4-(4-aminophenoxy)phenyl]propane, methylenedianiline, etc., are used as a vulcanizing agent), which has a longer scorch time than that of the aliphatic diamine vulcanization system, has a defect that the vulcanization rate is lower. Therefore, vulcanization systems that can achieve both allow high speed vulcanization and non-scorch have been desired.

The vulcanization mechanism of the aliphatic diamine vulcanization system is considered here. As the aliphatic diamine, hexamethylenediamine carbamate (6-aminohexylcarbamic acid) $H_3N^+(CH_2)_6NHCOO^-$ is widely used for vulcanization of carboxyl group-containing acrylic rubber. In the vulcanization reaction, heat is applied to the vulcanizing agent compound, so that the protective group of the amino group of hexamethylenediamine undergoes pyrolysis decarboxylation at near 100° C. or higher to become hexamethylenediamine, which reacts with the crosslinkable functional groups, such as carboxyl groups, in the acrylic rubber to promote the vulcanization reaction. Therefore, it has a defect that the scorch time is short (inferior scorch stability). Moreover, one of reasons that hexamethylenediamine is used in the form of carbonate is that hexamethylenediamine is difficult to handle because it is highly hygroscopic and easily evaporates.

The carboxyl group-containing acrylic rubber also includes carboxyl group-containing ethylene acrylic rubber (Vamac G, produced by DuPont), specific carboxyl group-containing acrylic rubber (Denka ER, produced by Denka Co. Ltd.), and the like. These carboxyl group-containing acrylic rubbers also have a defect that the scorch time is short. Some of Patent Documents 1 to 10 show a high vulcanization rate and a long scorch time; however, in some of these cases, the compression set characteristics inevitably decreases.

Further, Patent Document 11, which was filed by the present applicant, discloses HMDA-Fmoc:

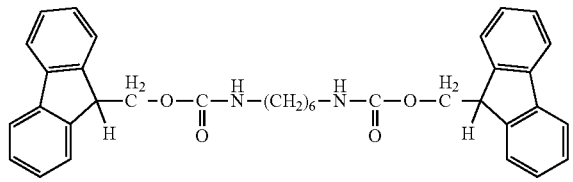

or HMDA-Dmoc:

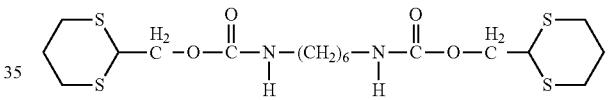

both of which are diurethane compounds represented by the general formula:

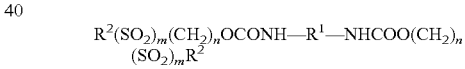

$R^1$: a $C_1$-$C_{20}$ divalent aliphatic alkylene group,
a divalent cycloaliphatic cycloalkylene group, or
a divalent aromatic group
$R^2$: a group that, on having a carbamate structure, decomposes by the action of a basic vulcanization accelerator to generate diamine
n: 0, 1, or 2
m: 0 or 1.

However, as shown in Comparative Examples 10 and 11 described later, it cannot be said that the tc10 and tc90 values are not sufficiently short, and that the ME (MH-ML) values are not sufficiently large.

PRIOR ART DOCUMENTS

Patent Documents

Patent Document 1: JP-A-11-255997
Patent Document 2: JP-A-11-100478
Patent Document 3: JP-A-11-140264
Patent Document 4: WO 2005/103143 A1
Patent Document 5: JP-A-2001-181464
Patent Document 6: JP-A-2001-316554
Patent Document 7: JP-A-2003-342437
Patent Document 8: JP-A-2002-317091

Patent Document 9: JP-A-2004-269873
Patent Document 10: JP-WO2003-4563 A1
Patent Document 11: WO 2009/096545 A1

OUTLINE OF THE INVENTION

Problem to be Solved by the Invention

An object of the present invention is to provide a diurethane compound that is used as a novel vulcanizing agent for crosslinkable group-containing acrylic rubber, and an acrylic rubber composition that contains the diurethane compound as a vulcanizing agent and that improves the delay of the vulcanization rate by scorch suppression, i.e., that satisfies both the excellent vulcanization rate of aliphatic diamines and the excellent scorch stability of aromatic diamines.

Means for Solving the Problem

The present invention provides a carbamate ester compound represented by the general formula:

Z—OCONH(CH$_2$)$_n$NHCOO—Z   [I]

wherein Z is [i], [ii], or [iii] below, and n is an integer of 2 to 10,

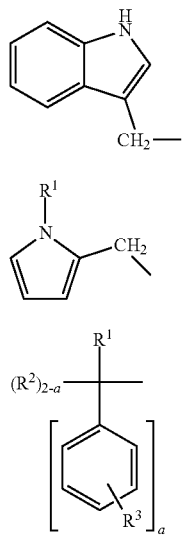

[i]

[ii]

[iii]

(wherein R$^1$ and R$^2$ are each independently a lower alkyl group having 1 to 5 carbon atoms, R$^3$ is a hydrogen atom or a lower alkyl group having 1 to 5 carbon atoms, and a is 1 or 2).

This carbamate ester compound is compounded into carboxyl group-containing acrylic rubber together with a vulcanization accelerator to form an acrylic rubber composition.

Effect of the Invention

The carbamate ester compound, which is the novel compound according to the present invention, is suitable as a vulcanizing agent for carboxyl group-containing acrylic rubber. In particular, a carboxyl group-containing acrylic rubber composition compounded with the carbamate ester compound and a basic vulcanization accelerator has a high vulcanization rate and excellent scorch stability, and allows short time injection molding etc., which have not been able to be realized in the conventional amine vulcanization systems.

Moreover, in vulcanization molding for extrusion molding application, in which the aromatic diamine vulcanization system was used because the aliphatic diamine vulcanization system could not be used in terms of scorching, the combined use with the carbamate ester compound of the present invention allows high speed vulcanization (short time vulcanization) and high temperature extrusion.

Therefore, the delay of the vulcanization rate by scorch suppression can be improved, and the setting range of molding conditions can be expanded by solving this problem that has been problematic during injection molding etc. Moreover, the vulcanizate physical properties, particularly compression set characteristics, are not significantly reduced. As a result, the carbamate ester compound of the present invention can be effectively applied to not only molding with mold, such as injection molding, compression molding, and transfer molding, but also extrusion molding, and can be effectively used in vulcanization molding of various seals such as oil seals, gaskets, and O rings, as well as hoses, diaphragms, rolls, rubber vibration insulators, industrial rubber parts, and the like.

EMBODIMENTS FOR CARRYING OUT THE INVENTION

In the general formula:

Z—OCONH(CH$_2$)$_n$NHCOO—Z   [I]

Z is [i], [ii], or [iii] below, and n is an integer of 2 to 10, preferably 6.

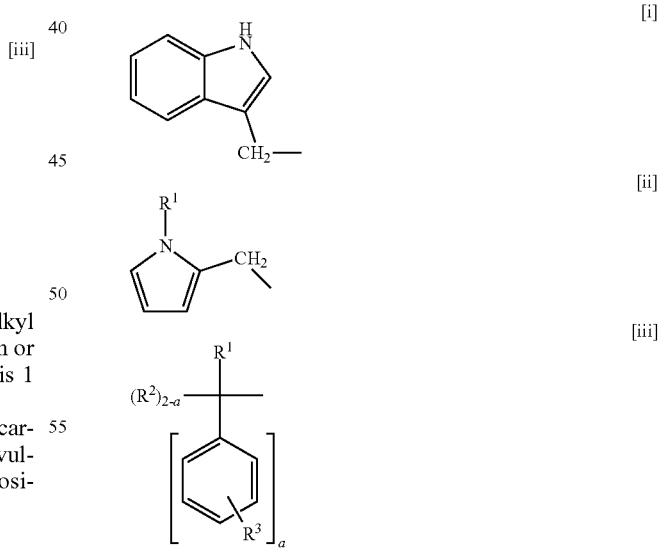

[i]

[ii]

[iii]

Such a carbamate ester compound having the substituent can be easily produced by reacting a linear alkylene diisocyanate ONC(CH$_2$)$_n$NCO and a hydroxyl group-containing compound, i.e., indolylmethanol, N-alkyl-2-hydroxymethylpyrrole, or a hydroxyl group-containing phenyl compound represented by the general formula:

[iv]

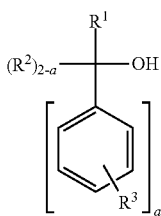

In the formula, $R^1$ and $R^2$ are each independently a lower alkyl group having 1 to 5 carbon atoms, $R^3$ is a hydrogen atom or a lower alkyl group having 1 to 5 carbon atoms, and a is 1 or 2.

Specifically, the carbamate ester compound is produced by the following reactions.

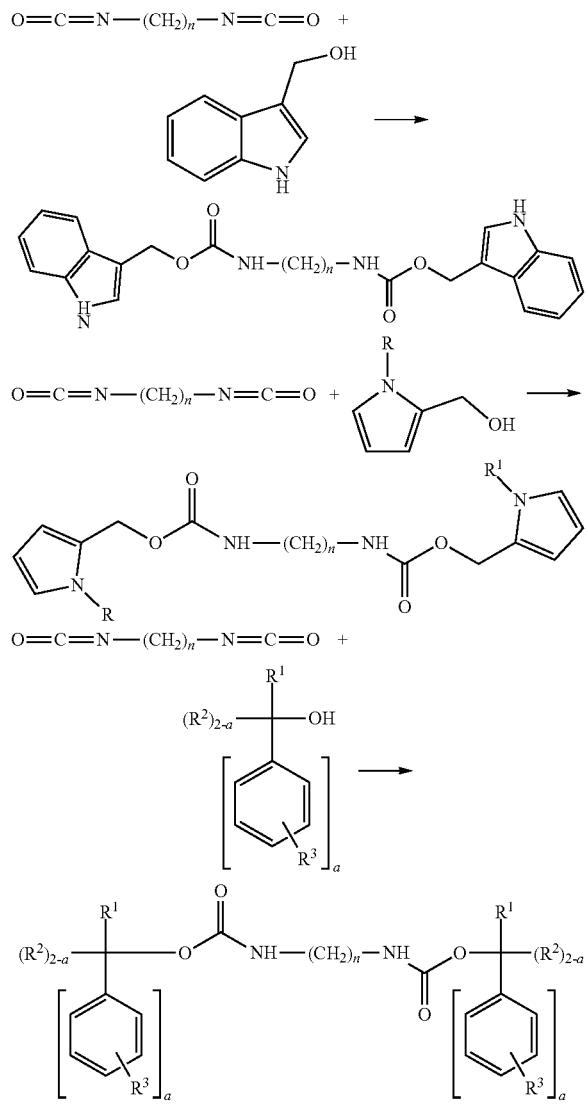

The linear alkylene diisocyanate and the hydroxyl group-containing compound are allowed to react at about 10 to 120° C. in an organic solvent, such as toluene, dioxane, or methyl ethyl ketone, and the insoluble portion is then filtered, thereby producing the carbamate ester compound.

These reactions can also be carried out in the presence of a urethane curing catalyst. Examples of the urethane curing catalyst include organic tin compounds, organic titanium compounds, organic zirconium compounds, and organic amine compounds. The organic amine compound and the organic tin compound can be used in combination. These are used at a ratio of about 0.1 to 10 parts by weight based on 100 parts by weight of the linear alkylene diisocyanate.

Examples of the organic tin compound used as a urethane curing catalyst include dibutyltin dilaurate, tin bis(2-ethylhexanoate), dibutyltin bis(2,4-pentanedionate), and the like. Examples of the organic titanium compound include titanium diisopropoxy-bis(ethylacetoacetate) and the like. Examples of the organic zirconium compound include zirconium dibutoxybis(ethylacetoacetate), zirconium tetra (acetylacetonate), and the like.

Moreover, examples of the organic amine compound include triethylenediamine, bis(dimethylaminoethyl)ether, 1,4-diazabicyclo[2.2.2]octane, pentamethyl diethylenetriamine, N,N-dimethylcyclohexylamine, N-methyldicyclohexylamine, N,N,N,N-tetramethylpropylenediamine, N,N,N,N-tetramethylhexamethylenediamine, N-methylmorpholine, N-ethylmorpholine, N,N-dimethylethanolamine, N,N-diethylethanolamine, 1,8-diazabicyclo [5.4.0]undecene-7 or organic acid salts thereof, 1,5-diazabicyclo[4.3.0]nonene-5, and the like. Examples of the organic acid salt of 1,8-diazabicyclo[5.4.0]undecene-7 include formate, 2-ethylhexanoate, phenolate, octanoate, p-toluenesulfonate, o-phthalate, etc., of 1,8-diazabicyclo[5.4.0]undecene-7.

The obtained carbamate ester compound is compounded, as a vulcanizing agent, into carboxyl group-containing acrylic rubber to form an acrylic rubber composition.

The carboxyl group-containing acrylic rubber usable herein is one obtained by copolymerizing at least one of alkyl acrylate containing an alkyl group having 1 to 8 carbon atoms and alkoxyalkyl acrylate containing an alkoxyalkyl group having 2 to 8 carbon atoms, with a carboxyl group-containing unsaturated compound.

Usable examples of alkyl acrylate include methyl acrylate, ethyl acrylate, propyl acrylate, isopropyl acrylate, n-butyl acrylate, n-hexyl acrylate, 2-ethylhexyl acrylate, and n-octyl acrylate, as well as methacrylates corresponding to these acrylates. In general, alkyl groups with a longer chain length are advantageous in terms of cold resistance, but are disadvantageous in terms of oil resistance. These characteristics tend to be reversed when the chain length becomes shorter. From the viewpoint of the balance between oil resistance and cold resistance, ethyl acrylate and n-butyl acrylate are preferably used.

Moreover, usable examples of alkoxyalkyl acrylate include methoxymethyl acrylate, 2-methoxyethyl acrylate, 2-ethoxyethyl acrylate, 2-n-butoxyethyl acrylate, 3-ethoxypropyl acrylate, and the like; preferably 2-methoxyethyl acrylate and 2-ethoxyethyl acrylate. Although alkoxyalkyl acrylate and alkyl acrylate can also be used singly, it is preferable that the former is used at a ratio of about 60 to 0 wt. %, while the latter is used at a ratio of about 40 to 100 wt. %. When alkoxyalkyl acrylate is copolymerized, the balance between oil resistance and cold resistance becomes excellent. However, if alkoxyalkyl acrylate is copolymerized at a ratio larger than the above range, the normal state physical properties and heat resistance tend to decrease.

Examples of the carboxyl group-containing unsaturated compound include monoalkyl (such as methyl, ethyl, propyl, isopropyl, n-butyl, and isobutyl) esters of maleic acid or fumaric acid; monoalkyl (such as methyl, ethyl, propyl, isopropyl, n-butyl, and isobutyl) esters of itaconic acid or citraconic acid; and the like. Mono-n-butyl maleate, mono-ethyl fumarate, and mono-n-butyl fumarate are preferably used. Such a carboxyl group-containing unsaturated compound is used at a copolymerization ratio of about 0.5 to 10 wt. %, preferably about 1 to 7 wt. %, in the carboxyl group-containing acrylic elastomer. If the copolymerization ratio is less than this range, vulcanization is insufficient and the compression set value is deteriorated. In contrast, if the copolymerization ratio is higher than this range, scorching is likely to occur. Since the copolymerization reaction is carried out so that the polymerization conversion rate is 90% or more, the charged monomer weight ratio corresponds almost to the copolymerization composition weight ratio of the generated copolymer.

In the carboxyl group-containing acrylic elastomer, another copolymerizable ethylenically unsaturated monomer can be further copolymerized at a ratio of about 50 wt. % or less. Examples thereof include styrene, α-methylstyrene, vinyl toluene, vinyl naphthalene, acrylonitrile, methacrylonitrile, amide acrylate, vinyl acetate, cyclohexyl acrylate, benzyl acrylate, ethylene, propylene, piperylene, butadiene, isoprene, pentadiene, and the like.

Further, if necessary, polyfunctional (meth)acrylate or oligomer can be copolymerized for the purpose of improving kneading processability, extrusion processability, and the like. Examples thereof include di(meth)acrylates of alkylene glycols, such as ethylene glycol, propylene glycol, 1,4-butanediol, 1,6-hexanediol, and 1,9-nonanediol; di(meth)acrylates of neopentyl glycol, tetraethylene glycol, tripropylene glycol, polypropylene glycol and the like; bisphenol A-ethylene oxide adduct diacrylate; dimethylol tricyclodecane diacrylate; glycerol methacrylate acrylate; 3-acryloyloxyglycerol monomethacrylate; and the like. Here, "(meth)acrylate" refers to acrylate or methacrylate.

The carbamate ester compound as a vulcanizing agent is used at a ratio of about 0.1 to 10 parts by weight, preferably about 0.5 to 5 parts by weight, based on 100 parts by weight of the carboxyl group-containing acrylic elastomer. If the vulcanizing agent is used at a ratio less than this range, vulcanization is insufficient, and sufficient physical properties are not obtained in terms of tensile strength, compression set, etc. In contrast, if the vulcanizing agent is used at a ratio larger than this range, the elongation at break is reduced, and the compression set is deteriorated.

A basic vulcanization accelerator can also be used in combination with the carbamate ester compound vulcanizing agent. The basic vulcanization accelerator used is a guanidine compound or a diazabicycloalkene compound, such as 1,8-diazabicyclo[5.4.0]undecene-7 and 1,5-diazabicyclo[4.3.0]nonene-5, or an organic acid salt or inorganic acid salt thereof. From the viewpoint of a higher addition effect, 1,8-diazabicyclo[5.4.0]undecene-7 is preferably used. Moreover, a mixture of 1,8-diazabicyclo[5.4.0]undecene-7 and silica can also be used. In practice, for example, Vulcofac ACT55, produced by Safic Alcan, is used.

Examples of the compound that forms an organic acid salt or inorganic acid salt of the diazabicycloalkene compound include hydrochloric acid, sulfuric acid, carboxylic acid, sulfonic acid, phenol, and the like. Examples of the carboxylic acid include octylic acid, oleic acid, formic acid, orthophthalic acid, adipic acid, and the like. Further, examples of the sulfonic acid include benzenesulfonic acid, toluenesulfonic acid, dodecylbenzenesulfonic acid, naphthalenesulfonic acid, and the like. These can be used singly or in combination of two or more.

Usable examples of the guanidine compound include guanidine or substituted guanidine, such as aminoguanidine, 1,1,3,3-tetramethylguanidine, n-dodecylguanidine, methylolguanidine, dimethylolguanidine, 1-phenylguanidine, 1,3-diphenylguanidine, 1,3-di-o-tolylguanidine, triphenylguanidine, 1-benzyl-2,3-dimethylguanidine, cyanoguanidine, and the like. In addition, 1,6-guanidinohexane, guanylurea, biguanide, 1-o-tolylbiguanide, and the like can also be used.

The guanidine compound as a basic vulcanization accelerator is used at a ratio of about 0.1 to 10 parts by weight, preferably about 0.3 to 6 parts by weight, based on 100 parts by weight of the carboxyl group-containing acrylic rubber. The diazabicycloalkene compound is used at a ratio of about 0.01 to 2 parts by weight, preferably about 0.05 to 1.0 parts by weight. Moreover, the organic acid salt or inorganic acid salt of the diazabicycloalkene compound is used at a ratio of about 0.1 to 5 parts by weight, preferably about 0.2 to 2 parts by weight, based on 100 parts by weight of the carboxyl group-containing acrylic rubber. If the basic vulcanization accelerator is used at a ratio larger than this range, the scorch time becomes short, which is not preferable.

The acrylic rubber composition is prepared by kneading carboxyl group-containing acrylic rubber and inorganic fillers such as carbon black and silica, lubricants, antioxidants, and other necessary compounding agents that are generally used as compounding agents for rubber, using a closed type kneading machine, such as a Banbury mixer, then adding a vulcanizing agent and a vulcanization accelerator, and mixing the resulting mixture using an open roll. The prepared acrylic rubber composition is generally vulcanized by press vulcanization (primary vulcanization) at about 150 to 200° C. for about 1 to 60 minutes, optionally followed by oven vulcanization (secondary vulcanization) at about 150 to 200° C. for about 1 to 10 hours.

EXAMPLES

The following describes the present invention with reference to Examples.

Example 1

In a 200 ml eggplant shaped flask, 11.00 g (74.7 mmol) of indolylmethanol (produced by Tokyo Chemical Industry Co., Ltd.) and 24 g of methyl ethyl ketone were charged, and stirred for dissolution in a water bath at 25° C. Then, 2 g of methyl ethyl ketone solution with 144 mg (0.228 mmol) of dibutyltin dilaurate (produced by FUJIFILM Wako Pure Chemical Corporation) dissolved therein was added. Subsequently, 24 g of methyl ethyl ketone solution with 6.00 g (35.6 mmol) of hexamethylene diisocyanate (produced by Tokyo Chemical Industry Co., Ltd.) was added dropwise in 2 or 3 batches, and the mixture was allowed to stand for 5 minutes.

After the completion of the reaction, the resultant was dried under reduced pressure at room temperature for 5 hours, thereby obtaining 17.24 g of a light brown crude powdered solid [carbamate ester compound A].

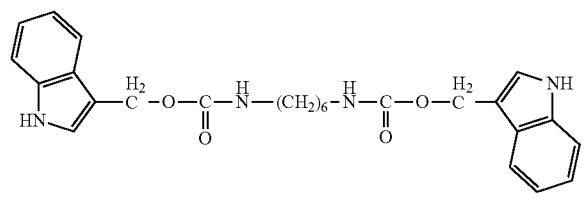

The structure of the obtained solid was identified using $^1$H NMR (Aceton-d$_6$) and FT-IR.

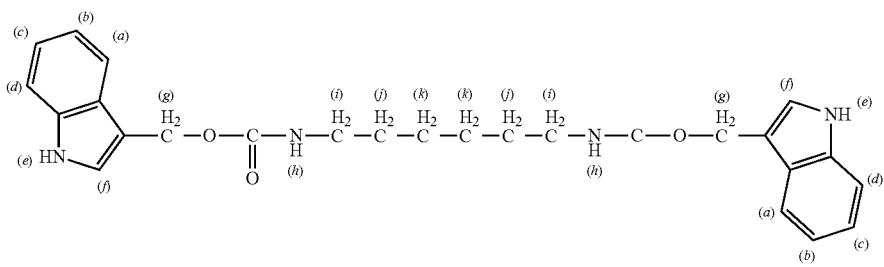 [SMILES: O=C(NCCCCCCNCOCc1c[nH]c2ccccc12)OCc1c[nH]c2ccccc12]

$^1$H NMR: (a) 7.7 ppm (d 2H)
(b) 7.1 ppm (t 2H)
(c), (d) 7.4 ppm (m 4H)
(e) 10.2 ppm (s 2H)
(f) 7.0 ppm (t 2H)
(g) 5.3 ppm (s 4H)
(h) 6.1 ppm (s 2H)
(i) 3.1 ppm (q 4H)
(j) 1.5 ppm (m 4H)
(k) 1.3 ppm (m 4H)
FT-IR: 3385 cm$^{-1}$: N—H stretching vibration of secondary heteroaromatic amine
3324 cm$^{-1}$: N—H stretching vibration derived from urethane bond
1686 cm$^{-1}$: C═O stretching vibration derived from urethane bond Example 2

In a 50 ml eggplant shaped flask, 6.23 g (56.1 mmol) of N-methyl-2-hydroxymethylpyrrole (produced by Tokyo Chemical Industry Co., Ltd.) was charged, and 2 g of methyl ethyl ketone solution with 108 mg (0.171 mmol) of dibutyltin dilaurate dissolved therein was added. Subsequently, 6 g of methyl ethyl ketone solution with 4.50 g (26.7 mmol) of hexamethylene diisocyanate dissolved therein was added dropwise, and the mixture was stirred in a water bath at 25° C. for 1.5 hours.

After the completion of the reaction, the resultant was dried under reduced pressure at room temperature for 8 hours, thereby obtaining 10.79 g (yield: 99%) of a light brown powdered solid [carbamate ester compound B].

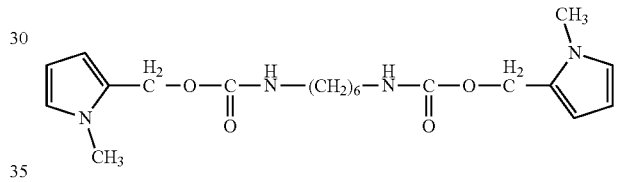

The structure of the obtained solid was identified using $^1$H NMR and FT-IR.

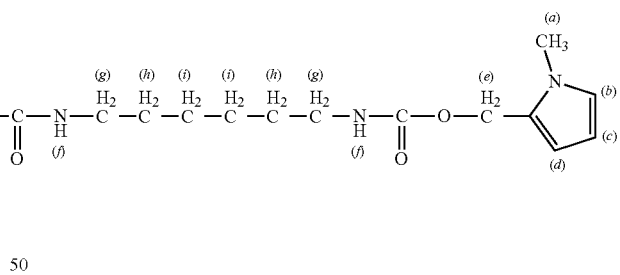

$^1$H NMR: (a) 3.6 ppm (s 6H)
(b) 6.6 ppm (t 2H)
(c) 6.2 ppm (q 2H)
(d) 6.1 ppm (t 2H)
(e) 5.0 ppm (s 4H)
(f) 6.6 ppm (s 2H)
(g) 3.1 ppm (m 4H)
(h) 1.5 ppm (m 4H)
(i) 1.3 ppm (m 4H)

FT-IR: 3325 cm$^{-1}$: N—H stretching vibration derived from urethane bond
1679 cm$^{-1}$: C═O stretching vibration derived from urethane bond

Example 3 (Referential Example)

In a 100 ml two-necked eggplant shaped flask, 11.16 g (56.25 mmol) of 1,1-diphenylethanol (produced by Tokyo Chemical Industry Co., Ltd.) was charged, and 2 g of methyl ethyl ketone solution with 360 mg (0.570 mmol) of dibutyltin dilaurate dissolved therein was added. Subsequently, 4 g of methyl ethyl ketone solution with 4.50 g (26.7 mmol) of hexamethylene diisocyanate dissolved therein was added dropwise, and the mixture was stirred for 5.5 hours in the reactor warmed at 80° C.

After the completion of the reaction, the insoluble portion was filtered and washed with n-hexane, and the filtrate was dried under reduced pressure at room temperature for 8 hours, thereby obtaining 14.25 g (yield: 94%) of a white powdered solid [carbamate ester compound C].

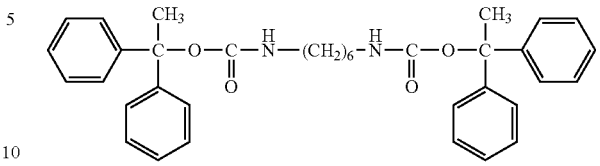

The structure of the obtained solid was identified using $^1$H NMR and FT-IR.

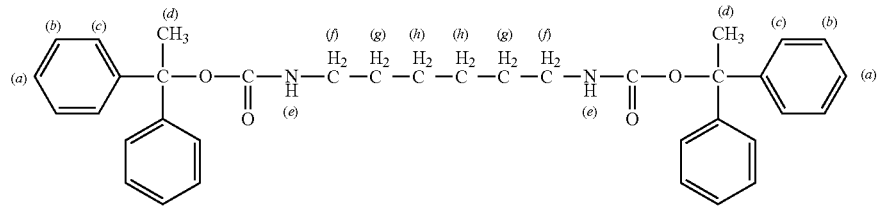 [SMILES: CC(OC(=O)NCCCCCCNC(=O)OC(C)(c1ccccc1)c1ccccc1)(c1ccccc1)c1ccccc1]

$^1$H NMR: (a), (b), (c) 7.2-7.3 ppm (m 20H)
(d) 2.2 ppm (s 6H)
(c), (d) 7.4 ppm (m 4H)
(e) 4.8 ppm (s 2H)
(f) 3.0 ppm (m 4H)
(g) 1.4 ppm (m 4H)
(h) 1.2 ppm (m 4H)
FT-IR: 3281 cm$^{-1}$: N—H stretching vibration derived from urethane bond
1690 cm$^{-1}$: C=O stretching vibration derived from urethane bond

Example 4 (Referential Example)

In a 50 ml eggplant shaped flask, 8.43 g (56.1 mmol) of α,α, 4-trimethyl-dimethylbenzyl alcohol (produced by Tokyo Chemical Industry Co., Ltd.), 360 mg (0.570 mmol) of dibutyltin dilaurate, and 4.50 g (26.7 mmol) of hexamethylene diisocyanate were charged, and the mixture was stirred for 2.5 hours in the reactor warmed at 80° C.

After the completion of the reaction, the resultant was cooled, thereby obtaining 12.06 g (yield: 91%) of a white powdered solid [carbamate ester compound D].

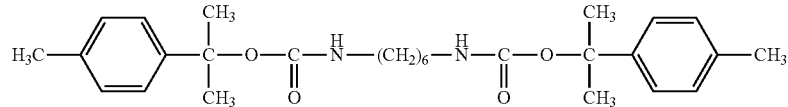

The structure of the obtained solid was identified using $^1$H NMR and FT-IR.

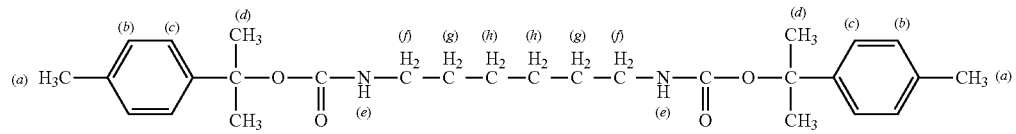

$^1$H NMR: (a) 2.3 ppm (s 6H)
(b) 7.1 ppm (t 2H)
(c) 7.2 ppm (m 4H)
(d) 1.7 ppm (s 12H)
(e) 4.7 ppm (m 2H)
(f) 3.0 ppm (m 4H)
(g) 1.4 ppm (m 4H)
(h) 1.3 ppm (m 4H)

FT-IR: 3307 cm$^{-1}$: N—H stretching vibration derived from urethane bond 1687 cm$^{-1}$: C=O stretching vibration derived from urethane bond

Example 5

| | |
|---|---|
| Carboxyl group-containing acrylic rubber (Noxtite PA-522HF, produced by Ummatec Co., Ltd.) | 100 parts by weight |
| FEF carbon black (Seast G-SO, produced by Tokai Carbon Co., Ltd.) | 55 parts by weight |
| Stearic acid (DTST, produced by Miyoshi Oil & Fat Co., Ltd.) | 1 part by weight |
| 4,4'-(α,α-dimethylbenzyl)diphenylamine (Nocrac CD, produced by Ouchi Shinko Chemical Industrial Co., Ltd.) | 2 parts by weight |
| Carbamate ester compound A | 1.7 parts by weight |
| 1,3-Di-o-tolylguanidine (Nocceler DT, produced by Ouchi Shinko Chemical Industrial Co., Ltd.) | 2 parts by weight |

Among the above components, the components other than the vulcanizing agent and the vulcanization accelerator were each kneaded with a Banbury mixer. Then, the vulcanizing agent and the vulcanization accelerator were added using an open roll. The acrylic rubber composition prepared in this manner was vulcanized by press vulcanization (primary vulcanization) at 180° C. for 8 minutes and oven vulcanization (secondary vulcanization) at 175° C. for 4 hours.

The vulcanization characteristics and vulcanizate physical properties of the compound, which was the acrylic rubber composition, were measured as described below.

Mooney scorch test: according to JIS K6300-1 corresponding to ISO 289 (125° C.)

The longer the t5 value (unit: minute), the less concern of compound scorch during molding and the less defects caused by scorching.

In general, when the t5 value is 10 minutes or more, defects caused by scorching during injection molding, compression molding or extrusion molding decrease.

$ML_{min}$: This is the minimum value of the Mooney viscosity and becomes an index of processability Vulcanization test: according to JIS K6300-2 corresponding to ISO 6502 (180° C., 12 minutes)

Rotorless Rheometer RLR-3, produced by Toyo Seiki Seisaku-sho, Ltd., was used.

ML: Minimum torque
MH: Maximum torque
tc10: Time required for vulcanization torque to reach ML+(MH−ML)×0.1
tc90: Time required for vulcanization torque to reach ML+(MH−ML)×0.9

Evaluation of the vulcanization rate can be determined by tc10, tc90, and ME (MH-ML) in the vulcanization test. The vulcanization rate is higher as tc10 and tc90 are shorter and ME is larger.

Normal state value: according to JIS K6251 corresponding to ISO 37, and JIS K6253 corresponding to ISO 7619-1

Compression set: according to JIS K6262 corresponding to ISO 815-1 (175° C., 70 hours)

Air oven aging test: according to JIS K6257 corresponding to ISO 188 (175° C., 70 hours); normal state value changes were measured.

Example 6

In Example 5, 1.5 parts by weight of the carbamate ester compound B was used in place of the carbamate ester compound A.

Example 7

In Example 5, 2.1 parts by weight of the carbamate ester compound C was used in place of the carbamate ester compound A.

Example 8

In Example 5, 1.8 parts by weight of the carbamate ester compound D was used in place of the carbamate ester compound A.

Comparative Example 1

In Example 5, 0.6 parts by weight of an aliphatic amine vulcanizing agent (CHEMINOX AC-6F, produced by Unimatec Co., Ltd.) was used in place of the carbamate ester compound A.

Comparative Example 2

In Example 5, 1.2 parts by weight of an aromatic diamine vulcanizing agent (CHEMINOX CLP5000, produced by Unimatec Co., Ltd.) was used in place of the carbamate ester compound A.

Comparative Example 3

In Comparative Example 1, 1 part by weight of stearylamine (Farmin 80S, produced by Kao Corporation) was further used as a vulcanization retarder.

Example 9

In Example 7, 1 part by weight of 1,8-diazabicyclo[5.4.0]undecene-7 dibasic acid salt-amorphous silica (weight ratio 70:30) mixture (Vulcofac ACT55, produced by Safic Alcan) was used as a vulcanization accelerator, in place of 1,3-di-o-tolylguanidine.

Example 10

In Example 8, 1 part by weight of 1,8-diazabicyclo[5.4.0]undecene-7 dibasic acid salt-amorphous silica (weight ratio 70:30) mixture (Vulcofac ACT55) was used as a vulcanization accelerator, in place of 1,3-di-o-tolylguanidine.

Comparative Example 4

In Comparative Example 1, 1 part by weight of 1,8-diazabicyclo[5.4.0]undecene-7 dibasic acid salt-amorphous silica (weight ratio 70:30) mixture (Vulcofac ACT55) was used as a vulcanization accelerator, in place of 1,3-di-o-tolylguanidine.

Comparative Example 5

In Comparative Example 3, 1 part by weight of 1,8-diazabicyclo[5.4.0]undecene-7 dibasic acid salt-amorphous silica (weight ratio 70:30) mixture (Vulcofac ACT55) was used as a vulcanization accelerator, in place of 1,3-di-o-tolylguanidine.

Following Table 1 shows the results obtained respectively in the above Examples 5 to 10 and Comparative Examples 1 to 5.

Comparative Example 6

In Comparative Example 1, 1 part by weight of 1,8-diazabicyclo[5.4.0]undecene-7 (Rhenogran XLA-60) was used as a vulcanization accelerator, in place of 1,3-di-o-tolylguanidine.

TABLE 1

| Measurement item | Example 5 | Example 6 | Example 7 | Example 8 | Comparative Example 1 | Comparative Example 2 | Comparative Example 3 | Example 9 | Example 10 | Comparative Example 4 | Comparative Example 5 |
|---|---|---|---|---|---|---|---|---|---|---|---|
| Mooney scorch test | | | | | | | | | | | |
| $ML_{min}$ (pts) | 33 | 32 | 29 | 29 | 32 | 32 | 32 | 29 | 28 | 36 | 36 |
| t5 (min) | 7.9 | 8.0 | 18.6 | 26.3 | 6.8 | 13.5 | 8.1 | 17.4 | 18.3 | 5.4 | 6.2 |
| Vulcanization test | | | | | | | | | | | |
| tc10 (min) | 0.60 | 0.62 | 0.89 | 1.12 | 0.58 | 1.19 | 0.69 | 0.99 | 1.05 | 0.51 | 0.59 |
| tc90 (min) | 4.69 | 6.34 | 6.09 | 6.58 | 4.26 | 8.25 | 6.54 | 6.94 | 7.14 | 5.08 | 6.46 |
| ML (N·m) | 0.14 | 0.13 | 0.12 | 0.12 | 0.13 | 0.13 | 0.13 | 0.13 | 0.12 | 0.14 | 0.14 |
| MH (N·m) | 0.71 | 0.69 | 0.76 | 0.71 | 0.78 | 0.35 | 0.64 | 0.78 | 0.75 | 0.82 | 0.67 |
| ME(MH − ML) (N·m) | 0.57 | 0.56 | 0.64 | 0.59 | 0.65 | 0.22 | 0.51 | 0.65 | 0.63 | 0.68 | 0.53 |
| Normal state value | | | | | | | | | | | |
| Hardness (Duro A) | 63 | 66 | 65 | 61 | 61 | 67 | 63 | 66 | 65 | 61 | 64 |
| 100% Modulus (MPa) | 4.1 | 5.0 | 4.9 | 4.1 | 3.7 | 4.8 | 3.5 | 5.2 | 4.7 | 4.3 | 4.0 |
| Breaking Strength (MPa) | 11.2 | 12.0 | 10.8 | 10.5 | 11.4 | 11.9 | 10.8 | 11.5 | 11.4 | 11.9 | 11.3 |
| Elongation at break (%) | 250 | 210 | 220 | 250 | 240 | 220 | 270 | 200 | 210 | 210 | 230 |
| Compression set | | | | | | | | | | | |
| 175° C., 70 hrs (%) | 14 | 18 | 16 | 16 | 12 | 15 | 23 | 19 | 16 | 13 | 20 |
| Normal state value changes after 70 hrs at 175° C. | | | | | | | | | | | |
| Hardness (Duro A) | +2 | +2 | +2 | +4 | +2 | +2 | −3 | +1 | +1 | +3 | +2 |
| 100% Modulus (MPa) | −23 | −20 | −15 | −11 | −12 | −5 | −16 | −14 | −21 | −18 | −20 |
| Breaking Strength (MPa) | 18 | −12 | −9 | −10 | −16 | −9 | −18 | −15 | −17 | −19 | −18 |
| Elongation at break (%) | +20 | +14 | +18 | +4 | +13 | 0 | +7 | +20 | +14 | +19 | +17 |

Example 11

In Example 6, 1 part by weight of 1,8-diazabicyclo[5.4.0]undecene-7 (Rhenogran XLA-60, produced by LANXESS) was used as a vulcanization accelerator, in place of 1,3-di-o-tolylguanidine.

Example 12

In Example 7, 1 part by weight of 1,8-diazabicyclo[5.4.0]undecene-7 (Rhenogran XLA-60) was used as a vulcanization accelerator, in place of 1,3-di-o-tolylguanidine.

Example 13

In Example 8, 1 part by weight of 1,8-diazabicyclo[5.4.0]undecene-7 (Rhenogran XLA-60) was used as a vulcanization accelerator, in place of 1,3-di-o-tolylguanidine.

Comparative Example 7

In Comparative Example 3, 1 part by weight of 1,8-diazabicyclo[5.4.0]undecene-7 (Rhenogran XLA-60) was used as a vulcanization accelerator, in place of 1,3-di-o-tolylguanidine.

Example 14

In Example 7, 0.5 part by weight of 1,8-diazabicyclo[5.4.0]undecene-7 (DBU produced by San-Apro Ltd.) was used as a vulcanization accelerator, in place of 1,3-di-o-tolylguanidine.

Example 15

In Example 8, 0.5 part by weight of 1,8-diazabicyclo[5.4.0]undecene-7 (DBU) was used as a vulcanization accelerator, in place of 1,3-di-o-tolylguanidine.

Comparative Example 8

In Comparative Example 1, 0.5 part by weight of 1,8-diazabicyclo[5.4.0]undecene-7 (DBU) was used as a vulcanization accelerator, in place of 1,3-di-o-tolylguanidine.

Comparative Example 9

In Comparative Example 3, 0.5 part by weight of 1,8-diazabicyclo[5.4.0]undecene-7 (DBU) was used as a vulcanization accelerator, in place of 1,3-di-o-tolylguanidine.

Comparative Example 10

In Example 5, the amount of FEF carbon black was changed to 60 parts by weight, and 1.5 parts by weight of HMDA-Fmoc was used in place of the carbamate ester compound A.

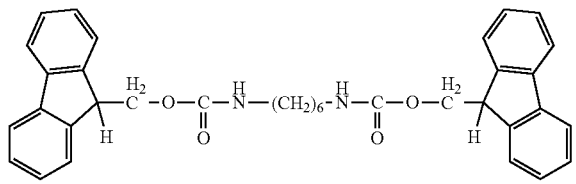

Comparative Example 11

In Example 5, the amount of FEF carbon black was changed to 60 parts by weight, and 1.5 parts by weight of HMDA-Dmoc was used in place of the carbamate ester compound A.

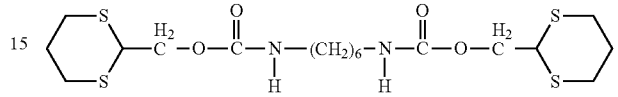

Following Table 2 shows the results obtained respectively in the above Examples 11 to 15 and Comparative Examples 6 to 11.

TABLE 2

| Measurement item | Example | | | Comparative Example | | Example | | Comparative Example | | | |
|---|---|---|---|---|---|---|---|---|---|---|---|
| | 11 | 12 | 13 | 6 | 7 | 14 | 15 | 8 | 9 | 10 | 11 |
| Mooney scorch test | | | | | | | | | | | |
| $ML_{min}$ (pts) | 34 | 30 | 30 | 38 | 36 | 35 | 34 | 41 | 37 | 36 | 36 |
| t5 (min) | 9.3 | 24.6 | 25.2 | 6.0 | 7.8 | 18.0 | 23.3 | 4.0 | 5.2 | >60 | >60 |
| Vulcanization test | | | | | | | | | | | |
| tc10 (min) | 0.83 | 1.24 | 1.30 | 0.65 | 0.70 | 1.08 | 1.20 | 0.36 | 0.47 | 2.74 | 1.65 |
| tc90 (min) | 7.39 | 7.39 | 7.52 | 6.31 | 7.25 | 6.33 | 6.62 | 3.53 | 4.79 | 9.20 | 8.92 |
| ML (N·m) | 0.13 | 0.12 | 0.12 | 0.14 | 0.14 | 0.13 | 0.13 | 0.15 | 0.14 | 0.16 | 0.15 |
| MH (N·m) | 0.70 | 0.70 | 0.67 | 0.77 | 0.63 | 0.82 | 0.81 | 0.88 | 0.69 | 0.41 | 0.32 |
| ME(MH − ML) (N·m) | 0.57 | 0.58 | 0.55 | 0.63 | 0.49 | 0.69 | 0.68 | 0.73 | 0.55 | 0.25 | 0.17 |
| Normal state value | | | | | | | | | | | |
| Hardness (Duro A) | 66 | 65 | 64 | 61 | 62 | 69 | 66 | 65 | 66 | 65 | 62 |
| 100% Modulus (MPa) | 4.9 | 4.5 | 4.2 | 4.5 | 3.9 | 5.9 | 5.1 | 5.7 | 4.3 | 2.5 | 2.8 |
| Breaking Strength (MPa) | 10.8 | 11.0 | 10.3 | 11.7 | 11.3 | 11.7 | 11.4 | 12.3 | 11.6 | 9.2 | 8.9 |
| Elongation at break(%) | 200 | 230 | 220 | 220 | 230 | 190 | 200 | 180 | 220 | 310 | 340 |
| Compression set | | | | | | | | | | | |
| 175° C., 70 hrs (%) | 23 | 24 | 20 | 16 | 22 | 23 | 19 | 15 | 21 | 15 | 26 |
| Normal state value changes after 70 hrs at 175° C. | | | | | | | | | | | |
| Hardness (Duro A) | +4 | +0 | +3 | +4 | +3 | +4 | +4 | +0 | +1 | — | — |
| 100% Modulus (MPa) | −15 | −21 | −2 | −20 | −13 | −29 | −16 | −30 | −19 | — | — |
| Breaking Strength (MPa) | −9 | −18 | −5 | −19 | −18 | −17 | −14 | −17 | −17 | — | — |
| Elongation at break (%) | +15 | +13 | +18 | +18 | +17 | +21 | +10 | +28 | +9 | — | — |

The invention claimed is:

1. A carbamate ester compound represented by the general formula:

Z—OCONH(CH$_2$)$_n$NHCOO—Z    [I]

wherein Z is [i] or [ii] below, and n is an integer of 2 to 10,

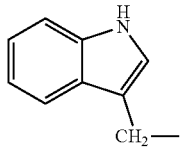 [i]

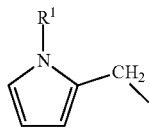 [ii]

wherein:
R$^1$ is a lower alkyl group having 1 to 5 carbon atoms.

2. The carbamate ester compound according to claim 1, wherein n in the formula [I] is 6.

3. The carbamate ester compound according to claim 1, which is used as a vulcanizing agent for carboxyl group-containing acrylic rubber.

4. An acrylic rubber composition compound comprising 0.1 to 10 parts by weight of a carbamate ester compound represented by the general formula:

Z—OCONH(CH$_2$)$_n$NHCOO—Z    [I]

wherein Z is [i], [ii], or [iii] below, and n is an integer of 2 to 10,

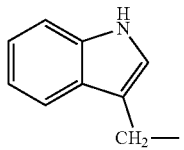 [i]

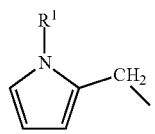 [ii]

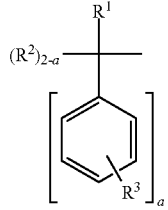 [iii]

wherein:
R$^1$ and R$^2$ are each independently a lower alkyl group having 1 to 5 carbon atoms,
R$^3$ is a hydrogen atom or a lower alkyl group having 1 to 5 carbon atoms, and
a is 1,
as a vulcanizing agent based on 100 parts by weight of carboxyl group-containing acrylic rubber.

5. The acrylic rubber composition according to claim 4, wherein 0.1 to 10 parts by weight of a guanidine compound vulcanization accelerator is further compounded.

6. The acrylic rubber composition according to claim 4, wherein 0.01 to 2 parts by weight of a diazabicycloalkene compound vulcanization accelerator is further compounded.

7. The acrylic rubber composition according to claim 4, wherein 0.1 to 5 parts by weight of an organic acid salts or inorganic acid salts of diazabicycloalkene compound vulcanization accelerator is further compounded.

8. A vulcanization molded article molded with mold from the acrylic rubber composition according to claim 4.

9. A vulcanization molded article extrusion-molded from the acrylic rubber composition according to claim 4.

* * * * *